(12) United States Patent
Hanson et al.

(10) Patent No.: US 11,813,443 B2
(45) Date of Patent: Nov. 14, 2023

(54) MAGNETIC COUPLER FOR HEMOSTATIC ROTOR SEALING

(71) Applicant: Boston Scientific Scimed, Inc., Maple Grove, MN (US)

(72) Inventors: Brian J. Hanson, Shoreview, MN (US); Steven R. Larsen, Lino Lakes, MN (US); Benjamin Breidall, Eden Prairie, MN (US); Joseph A. Kronstedt, New Hope, MN (US); Paul F. Chouinard, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 17 days.

(21) Appl. No.: 16/295,709

(22) Filed: Mar. 7, 2019

(65) Prior Publication Data

US 2019/0275224 A1 Sep. 12, 2019

Related U.S. Application Data

(60) Provisional application No. 62/640,740, filed on Mar. 9, 2018.

(51) Int. Cl.
*A61M 60/419* (2021.01)
*A61M 60/13* (2021.01)
(Continued)

(52) U.S. Cl.
CPC .......... *A61M 60/419* (2021.01); *A61M 60/13* (2021.01); *A61M 60/139* (2021.01);
(Continued)

(58) Field of Classification Search
CPC .............. A61M 60/135; A61M 60/205; A61M 60/268; A61M 60/419; A61M 60/857; A61M 1/1008
See application file for complete search history.

(56) References Cited

U.S. PATENT DOCUMENTS 5,021,048 A * 6/1991 Buckholtz ............. F04D 13/024
415/900
5,145,333 A * 9/1992 Smith ................... F04D 13/024
415/202
(Continued)

FOREIGN PATENT DOCUMENTS

CA 2663586 A1 3/2008
CN 101873870 A 10/2010
(Continued)

OTHER PUBLICATIONS

International Search Report and Written Opinion received for PCT Patent Application No. PCT/US2019/021162, dated Jun. 27, 2019, 11 pages.

*Primary Examiner* — Lynsey C Eiseman
*Assistant Examiner* — Amanda L Steinberg
(74) *Attorney, Agent, or Firm* — Faegre Drinker Biddle & Reath LLP

(57) ABSTRACT

Devices and methods for assisting blood flow are provided. The device includes a housing with an inlet and an outlet, and a fluid barrier separating the housing into a first section containing the inlet and outlet, and a second section. The device also includes an impeller shaft coupled to an impeller and a first magnet in the first section of the housing, and a drive shaft coupled to a second magnet in the second section of the housing. The first and second magnets are arranged such that rotation of the drive shaft rotates the second magnet causing rotation of the first magnet, which drives the impeller.

22 Claims, 17 Drawing Sheets

(51) Int. Cl.
*A61M 60/139* (2021.01)
*A61M 60/416* (2021.01)
*A61M 60/216* (2021.01)
*A61M 60/827* (2021.01)
*A61M 60/825* (2021.01)

(52) U.S. Cl.
CPC ........ *A61M 60/216* (2021.01); *A61M 60/416* (2021.01); *A61M 60/825* (2021.01); *A61M 60/827* (2021.01)

(56) References Cited

U.S. PATENT DOCUMENTS

| | | | |
|---|---|---|---|
| 6,056,520 A | 5/2000 | Nguyen et al. | |
| 6,176,822 B1 | 1/2001 | Nix et al. | |
| 6,176,848 B1 | 1/2001 | Rau et al. | |
| 9,398,743 B1* | 7/2016 | Fox | H02K 5/225 |
| 9,421,311 B2 | 8/2016 | Tanner et al. | |
| 9,616,157 B2 | 4/2017 | Akdis | |
| 9,737,652 B2 | 8/2017 | Larose et al. | |
| 2003/0233021 A1 | 12/2003 | Nose et al. | |
| 2006/0222533 A1* | 10/2006 | Reeves | A61M 1/3659 417/420 |
| 2009/0093764 A1* | 4/2009 | Pfeffer | A61M 1/1015 604/151 |
| 2009/0171137 A1 | 7/2009 | Farnan et al. | |
| 2011/0237863 A1* | 9/2011 | Ricci | A61M 1/1015 600/16 |
| 2011/0238172 A1 | 9/2011 | Akdis | |
| 2013/0338559 A1* | 12/2013 | Franano | A61M 60/531 604/4.01 |
| 2014/0010686 A1 | 1/2014 | Tanner et al. | |
| 2014/0336446 A1* | 11/2014 | Rodefeld | A61M 1/1036 600/16 |
| 2016/0271308 A1 | 9/2016 | Larose et al. | |
| 2017/0043074 A1* | 2/2017 | Siess | F04D 29/048 |

FOREIGN PATENT DOCUMENTS

| | | |
|---|---|---|
| CN | 101918675 A | 12/2010 |
| EP | 2061531 A2 | 5/2009 |
| JP | 11-244376 A | 9/1999 |
| JP | H11-244376 A | 9/1999 |
| JP | 2001-517102 A | 10/2001 |
| JP | 2009-197736 A | 9/2009 |
| JP | 2010-503495 A | 2/2010 |
| WO | 92/03181 A1 | 3/1992 |
| WO | 2008/034068 A2 | 3/2008 |
| WO | 2015/098709 A1 | 7/2015 |
| WO | 2018/226991 A1 | 12/2018 |

* cited by examiner

MAGNETIC COUPLER FOR HEMOSTATIC ROTOR SEALING

CROSS-REFERENCE TO RELATED APPLICATION

This application claims priority to Provisional Application No. 62/640,740, filed Mar. 9, 2018, which is herein incorporated by reference in its entirety.

TECHNICAL FIELD

The disclosure pertains to medical devices and more particularly to blood flow assist devices including an implantable rotary blood pump for assisting the heart in driving blood flow, and methods for using such medical devices.

BACKGROUND

A wide variety of medical devices have been developed for medical use including, for example, medical devices utilized to assist the heart in pumping blood throughout the circulatory system. These medical devices may be implanted temporarily or permanently and are manufactured and used according to any one of a variety of different methods. Of the known medical devices and methods, each has certain advantages and disadvantages. There is an ongoing need to provide alternative medical devices as well as alternative methods for manufacturing and using the medical devices.

SUMMARY

This disclosure provides design, material, manufacturing method, and use alternatives for medical devices. An example medical device includes a housing including at least one inlet for receiving blood flow, and at least one outlet for delivering blood flow, the housing having a longitudinal axis, a fluid barrier disposed within the housing and separating the housing into a first section containing the at least one inlet and the at least one outlet, and a second section, the fluid barrier being impervious to fluid, an impeller disposed within the first section of the housing, wherein a longitudinal axis of the impeller and the longitudinal axis of the housing are the same, the impeller having a main body and at least one blade extending radially outward from the main body, at least a first magnet coupled to an impeller shaft, the impeller shaft coupled to the impeller, the first magnet disposed in the first section of the housing and rotatably coupled to the impeller shaft, a drive shaft disposed within the second section of the housing, and at least a second magnet disposed on the drive shaft within the second section of the housing, the first and second magnets configured and arranged such that rotation of the second magnet causes the first magnet to rotate.

Alternatively or additionally to any of the embodiments above, the medical device further includes a power source coupled to the drive shaft.

Alternatively or additionally to any of the embodiments above, the power source is disposed within a catheter shaft attached to the second section of the housing.

Alternatively or additionally to any of the embodiments above, the power source is a motor.

Alternatively or additionally to any of the embodiments above, the power source is a second impeller connected to the drive shaft, wherein the catheter shaft defines a fluid pathway, wherein the drive shaft and second impeller are disposed within the fluid pathway such that a fluid impacting the second impeller drives the impeller which turns the second magnet, which causes the first magnet to turn, thereby turning the impeller shaft and impeller.

Alternatively or additionally to any of the embodiments above, the at least one outlet includes a plurality of side openings spaced apart around a circumference of the housing, wherein the impeller is positioned within the housing such that the at least one blade is disposed adjacent the plurality of side openings.

Alternatively or additionally to any of the embodiments above, the first magnet has a first opening therethrough configured for receiving and coupling the impeller shaft to the first magnet, the second magnet has a second opening therethrough configured for receiving and coupling the drive shaft to the second magnet, wherein the first and second openings each have a first transverse cross-sectional shape taken perpendicular to a longitudinal axis of the drive shaft, and the drive shaft and at least a portion of the impeller shaft each have a second transverse cross-sectional shape taken perpendicular to the longitudinal axis of the respective shafts, wherein the first and second transverse cross-sectional shapes are non-round, such that rotation of the impeller shaft and drive shaft causes rotation of the first and second magnets, respectively.

Alternatively or additionally to any of the embodiments above, the first and second transverse cross-sectional shapes are a stadium, with straight sides and semicircular ends.

Alternatively or additionally to any of the embodiments above, a distal region of the impeller shaft is cylindrical.

Alternatively or additionally to any of the embodiments above, a proximal end of the impeller shaft extends proximal of the first magnet, the proximal end having a first protrusion configured to be received by a first recess in the fluid barrier.

Alternatively or additionally to any of the embodiments above, the impeller shaft includes a disc adjacent the first protrusion, the disc extending perpendicularly from a longitudinal axis of the impeller shaft.

Alternatively or additionally to any of the embodiments above, the disc has two opposing lobes.

Alternatively or additionally to any of the embodiments above, the medical device further includes a pivot member disposed between the second magnet and the fluid barrier.

Alternatively or additionally to any of the embodiments above, the pivot member has a projection extending distally therefrom, the projection configured to be received by a second recess in the fluid barrier.

Alternatively or additionally to any of the embodiments above, the medical device further including a bearing assembly configured to support and center a distal end of the impeller shaft, the bearing assembly including a bearing housing fixed to the housing, a spacer slidably disposed within the bearing housing, and a distal bearing fixed within the spacer.

Alternatively or additionally to any of the embodiments above, the bearing assembly further includes a spring member disposed around the spacer.

Another example medical device includes a housing including an inlet for receiving blood flow, and a plurality of side openings for delivering blood flow, the housing having a longitudinal axis, a fluid barrier disposed within the housing and separating the housing into a first section containing the inlet and the plurality of side openings, and a second section, the fluid barrier being impervious to fluid, an impeller disposed within the first section of the housing, wherein a longitudinal axis of the impeller and the longitudinal axis of the housing are the same, the impeller having a main body and at least one blade extending radially outward from the main body, at least a first magnet disposed in the first section of the housing and coupled to the impeller such that rotation of the first magnet causes rotation of the impeller, a drive shaft disposed within the second section of the housing, at least a second magnet coupled to the drive shaft and disposed within the second section of the housing, the first and second magnets configured and arranged such that rotation of the second magnet causes rotation of the first magnet, a catheter shaft coupled to the housing, and a power source coupled to the drive shaft, the power source disposed within the catheter shaft.

Alternatively or additionally to any of the embodiments above, the power source is a second impeller connected to the drive shaft, wherein the catheter shaft defines a fluid pathway, wherein the drive shaft and second impeller are disposed within the fluid pathway such that a fluid impacting the second impeller drives the impeller which turns the second magnet, which causes the first magnet to turn, thereby turning the impeller.

Alternatively or additionally to any of the embodiments above, the medical device further including an impeller shaft disposed within and coupled to the impeller and the first magnet, and a bearing assembly configured to support and center a distal end of the impeller shaft, the bearing assembly including a bearing housing fixed to the housing, a spacer slidably disposed within the bearing housing, and a distal bearing fixed within the spacer.

A method of assisting blood flow from a patient's heart into the patient's circulatory system includes inserting a device into an ascending aorta, the device including a housing including at least one inlet for receiving blood flow from a left ventricle of the heart, and at least one outlet for delivering blood flow into the ascending aorta, the housing having a longitudinal axis, a fluid barrier disposed within the housing and separating the housing into a first section containing the at least one inlet and the at least one outlet, and a second section, the fluid barrier being impervious to blood, an impeller disposed within the first section of the housing, wherein a longitudinal axis of the impeller and the longitudinal axis of the housing are the same, the impeller having a main body and at least one blade extending radially outward from the main body, an impeller shaft disposed within and coupled to the impeller, at least a first magnet having a first opening therethrough for receiving the impeller shaft, the first magnet disposed in the first section of the housing and rotatably coupled to the impeller shaft, a drive shaft disposed within the second section of the housing, and at least a second magnet disposed on the drive shaft within the second section of the housing, the first and second magnets configured and arranged such that rotation of the second magnet causes the first magnet to rotate. The method further includes rotating the drive shaft thereby rotating the second magnet, which causes rotation of the first magnet, thereby rotating the impeller shaft and the impeller, creating suction thereby drawing blood from the left ventricle through the at least one inlet into the housing and driving blood through the at least one outlet and into the ascending aorta.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
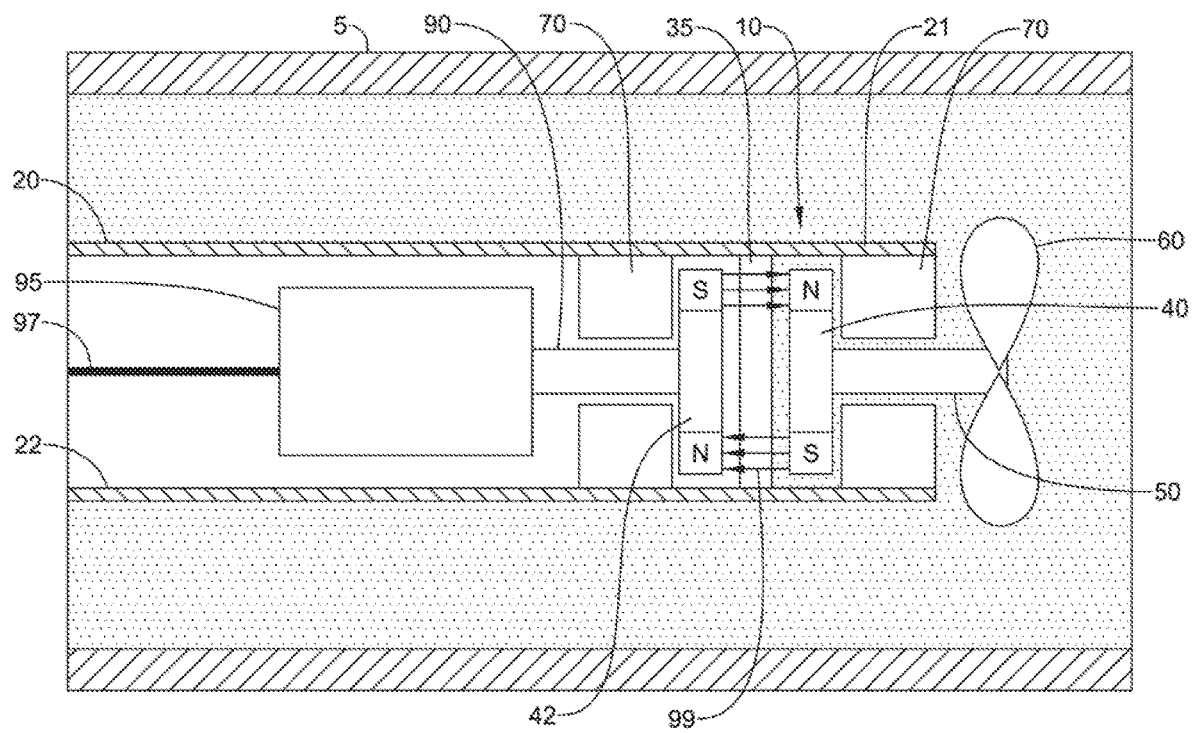
FIG. 1 illustrates an example mechanism for transferring forces across an impervious barrier.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

As will be described in greater detail below, FIG. 1 illustrates a partial cross-section of an example power transfer mechanism which may be utilized within a blood flow assist device. Specifically, FIG. 1 illustrates how magnetic forces transmitted through a blood impervious barrier may be used to drive an impeller for assisting blood flow through a blood vessel. In the illustration, a device 10 is positioned in a blood vessel 5. The device 10 may include a housing 20 separated into a distal first section 21 and a proximal second section 22 by a fluid barrier 35 that is impermeable to blood. In some examples, the fluid barrier 35 may be made of ultra-high molecular weight polyethylene (UHMWPE), polyoxymethylene such as Delrin® acetal homopolymer resin, polyether ether ketone (PEEK), nylon, high-density polyethylene (HDPE), or other polymers conventionally used in medical devices, sapphire, ruby, nickel-cobalt based alloys such as MP35N®, cobalt chromium alloys, titanium or titanium alloys. In other examples, the fluid barrier 35 may be fiber loaded or oil impregnated. The fluid barrier 35 may extend transversely across the interior of the housing 20 and provides a complete seal against blood leakage into the second section 22 when the first section 21 is filled with blood. The device 10 may further include a first magnet 40 disposed in the first section 21 of the housing 20 and coupled to an impeller shaft 50 and impeller 60. The first magnet 40 may be coupled to the impeller shaft 50 by a physical structure such as an opening within the first magnet 40 receiving the impeller shaft 50. Alternatively, the first magnet 40 may have a protrusion that is received within a recess in the impeller shaft 50. The opening/recess may be keyed to the shaft/protrusion to couple the magnet and shaft. For example, the opening/recess may have a shape matching the shape of shaft/protrusion. In other examples, the first magnet 40 may be coupled to the impeller shaft 50 by welding, sintering, bonding with adhesive, etc. The device may include one or more bearing 70 surrounding or supporting the impeller shaft.

In the second section 22 of the housing 20, a second magnet 42 may be coupled to a drive shaft 90 which may be coupled to a power source 95. The second magnet 42 may be coupled to the drive shaft 90 as discussed above with regard to the first magnet 40 and impeller shaft 50. The one or more bearing 70 may surround the drive shaft 90. In some examples, the power source 95 may be an electric motor with a power cord 97 extending proximally through the housing 20, through a catheter (not shown) connected to the housing, and outside the body.

In the example illustrated in FIG. 1, the first and second magnets 40, 42 are dipole magnets, with the north pole N of the first magnet 40 positioned across the fluid barrier 35 from the south pole S of the second magnet 42 and the south pole S of the first magnet 40 positioned across the fluid barrier 35 from the north pole N of the second magnet 42. This orientation of the first and second magnets 40, 42 ensures that the attractive magnetic force between the magnets, indicated by arrows 99, couples the rotational movement of the second magnet 42 with rotational movement of the first magnet 40. The magnetic force is transmitted through the fluid barrier 35. It will be understood that magnets with more than two poles may be used. In use, the power source 95 rotates the drive shaft 90 thereby rotating the second magnet 42, which in turn causes the first magnet 40 to rotate at the same speed as the second magnet 42. Rotation of the first magnet 40 rotates the attached impeller shaft 50 which rotates the attached impeller 60. The impeller 60 is in fluid contact with blood in the blood vessel 5, thus rotation of the impeller 60 assists blood flow through the blood vessel 5. The fluid barrier 35 prevents blood leakage into the second section 22 of the housing 20 and thus prevents blood contact with the drive shaft 90 and the power source 95.

Additionally, multiple magnets may be used on either side of the fluid barrier 35. Regardless of the number and/or type of magnet used, the magnet(s) are configured and positioned such that rotation of the magnet(s) connected to the drive shaft 90 and power source 95 causes rotation of the magnet(s) connected to the impeller 60.

Figure 2:
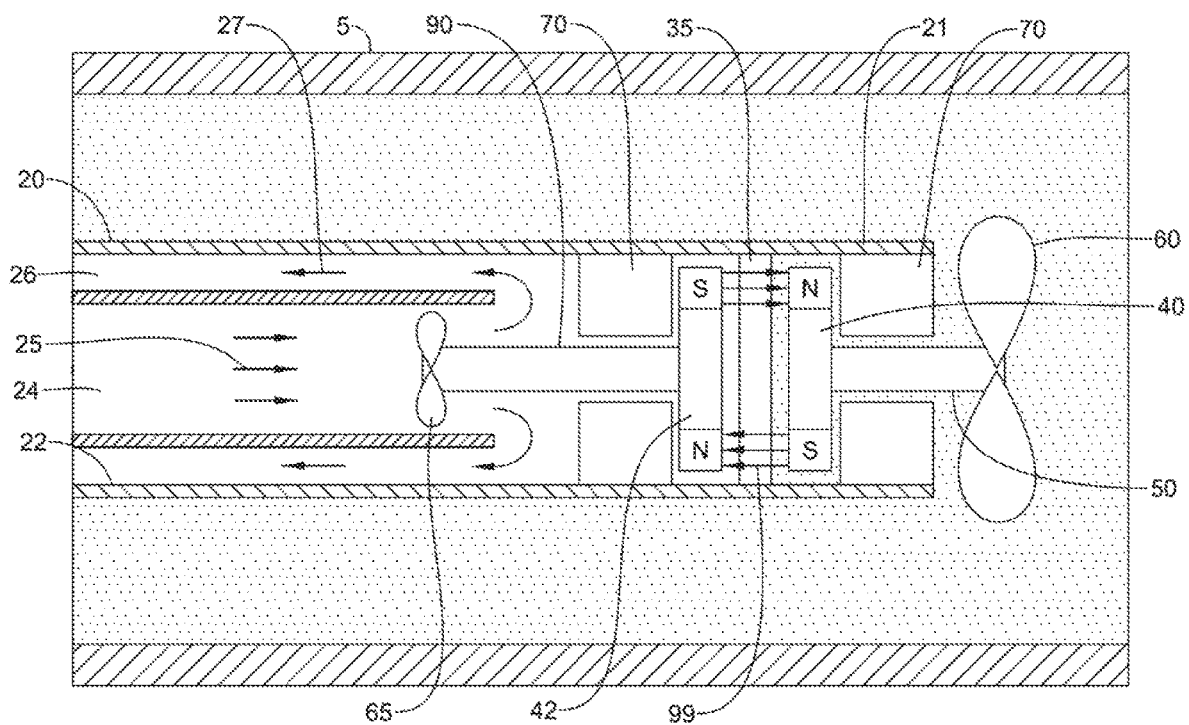
FIG. 2 illustrates another example mechanism for transferring forces across an impervious barrier.

FIG. 2 illustrates another example power transfer mechanism which may be utilized within a blood flow assist device. Specifically, FIG. 2 illustrates how magnetic forces transmitted through a blood impervious barrier may be used to assist blood flow through a vessel. The device illustrated in FIG. 2 is similar to that illustrated in FIG. 1 but with a fluid as the power source. It will be understood that the fluid source will be provided under pressure or vacuum, with the fluid flowing in a high or low pressure stream. One end of the drive shaft 90 may be connected to the second magnet 42 and a second end of the drive shaft 90 may be connected to a second impeller 65. The second section 22 of the housing 20, and the catheter (not shown) connected to the housing 20 may both include an inner lumen 24 and an outer lumen 26. A high or low pressure fluid such as saline or other suitable fluid may be injected through the inner lumen 24 towards the second impeller 65, as shown by arrows 25. The high or low pressure fluid turns the second impeller 65, which rotates the drive shaft 90 and the attached second magnet 42. As in the first example illustration in FIG. 1, rotation of the second magnet causes the first magnet 40 to rotate, thereby rotating the impeller shaft 50 and the impeller 60. The impeller 60 is in contact with blood in the blood vessel 5, thus rotation of the impeller 60 assists blood flow through the blood vessel 5. After turning the second impeller 65, the high or low pressure fluid then returns through the outer lumen 26, as shown by arrows 27. The fluid is prevented from entering the blood vessel 5 by the fluid barrier 35. Similarly, the fluid barrier 35 prevents blood from entering the second section 22 and mixing with the fluid. The high or low pressure fluid may be provided from a pressurized or vacuum source outside the body, and the return fluid may be collected and recycled outside the body.

Figure 3:
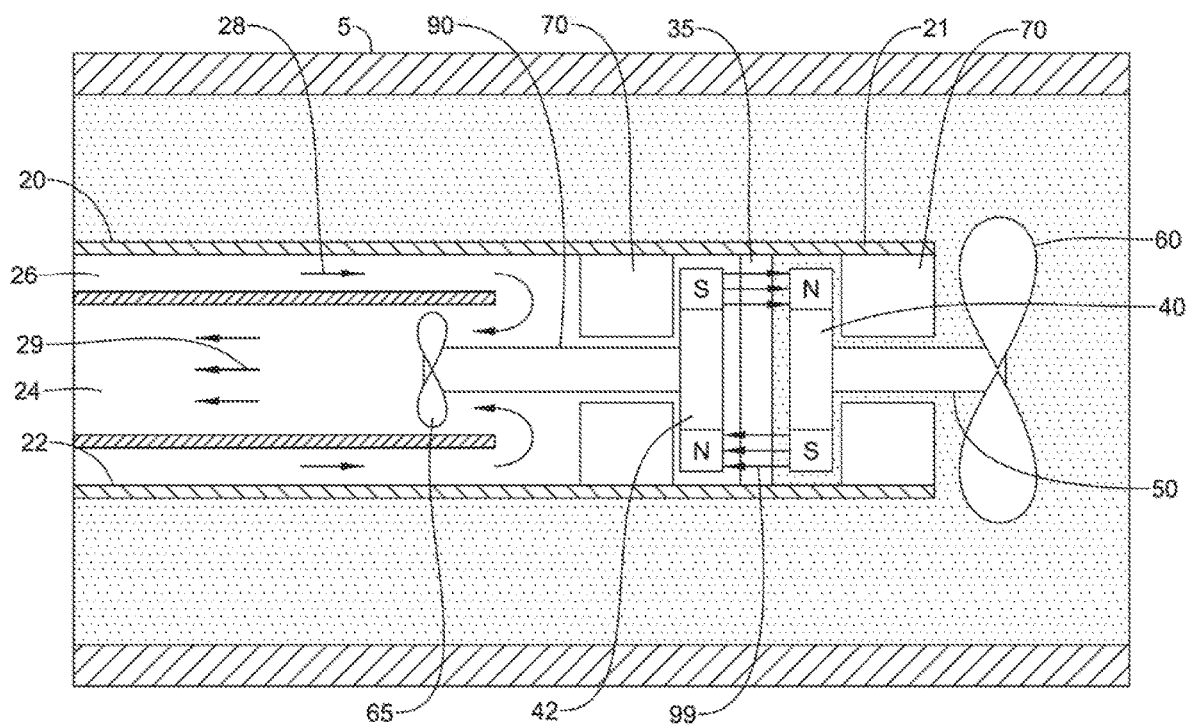
FIG. 3 illustrates another example mechanism for transferring forces across an impervious barrier.

FIG. 3 illustrates another example power transfer mechanism which may be utilized within a blood flow assist device. The device illustrated in FIG. 3 is similar to that illustrated in FIG. 2, but with the fluid direction reversed. Specifically, FIG. 3 illustrates how the high or low pressure fluid may be injected through the outer lumen 26 towards the second impeller 65, as shown by arrows 28. The high or low pressure fluid turns the second impeller 65, which rotates the drive shaft 90 and the attached second magnet 42. As in the first example illustration in FIG. 1, rotation of the second magnet causes the first magnet 40 to rotate, thereby rotating the impeller shaft 50 and the impeller 60. The impeller 60 is in contact with blood in the blood vessel 5, thus rotation of the impeller 60 assists blood flow through the blood vessel 5. After turning the second impeller 65, the high or low pressure fluid then returns through the inner lumen 24, as shown by arrows 29. The fluid is prevented from entering the blood vessel 5 by the fluid barrier 35. Similarly, the fluid barrier 35 prevents blood from entering the second section 22 and mixing with the fluid. The high or low pressure fluid may be provided from a source outside the body, and the return fluid may be collected and recycled outside the body. The fluid source may be pressurized or under vacuum.

Figure 4:
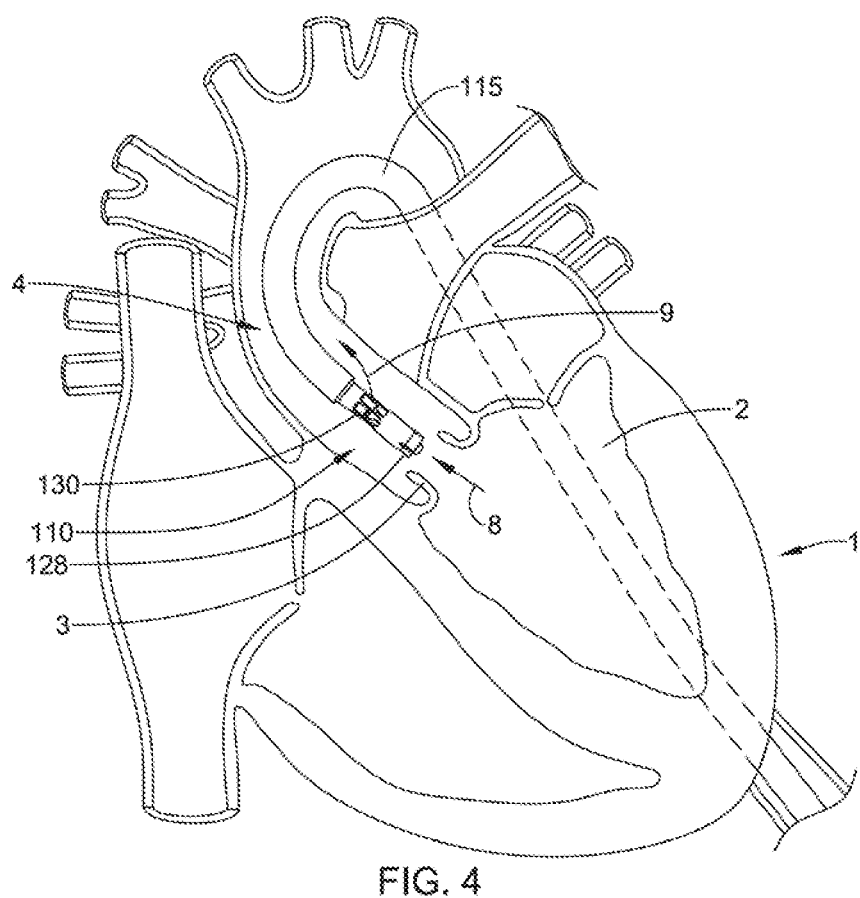
FIG. 4 illustrates an exemplary device for assisting blood flow, positioned within the heart.

FIG. 4 illustrates an example device 110 including a power transfer mechanism positioned within the heart 1 of a patient. As shown in FIG. 4, the device 110, connected to a catheter shaft 115, may be positioned in the ascending aorta 4 with the distal end 128 of the device 110 adjacent the aortic valve 3. This position may be beneficial as the blood (depicted by arrow 8) exiting the left ventricle 2 may enter the distal end 128 of the device 110 whereby the device 110 pumps the blood such that it exits the side openings 130 of the device 110 (the blood exiting the device 110 is depicted by arrow 9) with additional force than was provided solely by the left ventricle 2. It can be appreciated that the additional pumping action of the device 110 may assist the heart 1 in circulating blood throughout the body. Alternatively, the device 110 may be positioned across the aortic valve 3, with the distal end 128 of the device 110 within the left ventricle 2 and the side openings 130 in the ascending aorta 4. In a further example, the device 110 may be positioned with the side openings 130 in the descending aorta. It will also be appreciated that the size of the device 110 relative to the size of the heart chambers and aorta are not intended to be limiting and the size of the device 110 may be altered to provide a desired blood flow assist. The catheter shaft 115 connected to the device 110 may extend through the vasculature and outside the body. The catheter shaft 115 may contain a power cord connected to an external power source. It is also contemplated that the device 110 may include a power source, or a power source may be provided internal to the patient but remote from the device 110, such as an internal pacemaker.

It is noted that while the above discussion describes the benefits of utilizing the device 110 in the ascending aorta of the heart, it is contemplated that the device 110 may be utilized in other portions of the heart or other portions (e.g., other body lumens) of the body. In some examples, the device 110 may be inserted in the patient with the housing positioned in the descending aorta, upstream of the renal arteries. This position may provide increased blood flow to the kidneys. Alternatively, the device 110 may be positioned within a renal artery. A still further alternative is positioning the device 110 downstream of the renal arteries, just before the iliac bifurcation. In a further example, the device 110 may be positioned in the right ventricle, pumping blood across the pulmonary valve.

Figure 5:
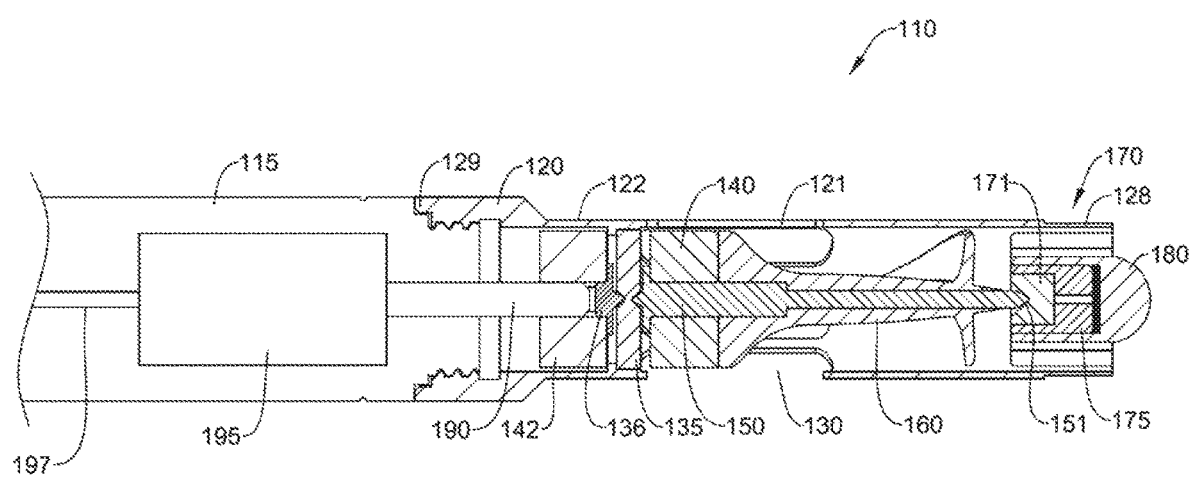
FIG. 5 is a cross sectional view of an exemplary device for assisting blood flow.

FIG. 5 illustrates a blood assist device 110 similar in form and function to the device shown in FIG. 4. In other words, FIG. 5 illustrates a blood assist device 110 that may be positioned with a blood vessel of a patient. Additionally, and as will be discussed in greater detail below, the blood assist device illustrated in FIG. 5 may include a power transfer mechanism described and illustrated in any of FIGS. 1-3.

The device 110 may include a catheter shaft 115 coupled to the proximal end 129 of a housing 120. The housing 120 may be separated into a distal first section 121 and a proximal second section 122 by a fluid barrier 135 that is impermeable to fluid, including blood. The first section 121 of the housing 120 may have at least one side opening 130 extending through the wall of the housing 120. The fluid barrier 135 may extend transversely across the interior of the housing 120 and provide a complete seal against blood leakage into the second section 122 when the first section 121 is filled with blood. The fluid barrier 135 further prevents any fluid in the second section 122 from entering the first section 121 where it could enter the blood stream. The device 110 may further include a first magnet 140 disposed in the first section 121 of the housing 120 and coupled to an impeller shaft 150 and an impeller 160. The first magnet 140 and impeller 160 may both be coupled to the impeller shaft 150 such that rotation of the first magnet 140 rotates the impeller shaft 150 which rotates the impeller 160. The impeller 160 may be a structure separate from the impeller shaft 150 and coupled to the impeller shaft 150. In some examples, the impeller shaft 150 may be disposed within the impeller 160. In other examples, the impeller 160 may be attached to the impeller shaft 150 by bonding, welding, molding, etc. Alternatively, the impeller 160 and impeller shaft 150 may be formed as a single monolithic structure. The impeller 160 may be disposed within the first section 121 of the housing 120, adjacent the side opening 130. The impeller shaft distal end 151 may be seated in a distal bearing assembly 170 disposed in the housing distal end 128. The distal bearing assembly 170 may be coupled to the housing 120 at discrete locations spaced apart circumferentially around the housing 120, thus allowing the distal end 128 to act as an inlet, receiving blood flow into the housing 120, around the distal bearing assembly 170. The side opening 130 may act as an outlet allowing blood flow to exit the housing. The housing 120 may have a single side opening 130 or a plurality of side openings 130. When a plurality of side openings 130 are present, they may be spaced apart circumferentially around a portion of or the entire circumference of the housing 120. The distal bearing assembly 170 may include a distal bearing 171, a spacer 175, and a bearing housing 180.

In the second section 122 of the housing 120, a second magnet 142 may be coupled to a drive shaft 190 which may be coupled to a power source 195. The device 110 may be devoid of any fluid disposed between the second magnet 142 and the drive shaft 190. In the example illustrated in FIG. 5, the power source 195 may be an electric motor with a power cord 197 extending proximally through the catheter shaft 115 and outside the body. Alternatively, the power source may be located outside the body or within the body but remote from the device 110. A pivot member 136 may provide an interface between the fluid barrier 135 and the second magnet 142. The fluid barrier 135, in addition to preventing fluid from passing between the first section 121 and second section 122 of the housing 120, may function as a thrust bearing against which the pivot member 136 and impeller shaft 150 rotate. In some examples, the fluid barrier 135 may be made of ultra-high molecular weight polyethylene (UHMWPE), polyoxymethylene such as Delrin® acetal homopolymer resin, polyether ether ketone (PEEK), nylon, high-density polyethylene (HDPE), or other polymers conventionally used in medical devices, sapphire, ruby, nickel-cobalt based alloys such as MP35N®, cobalt chromium alloys, titanium or titanium alloys. In other examples, the fluid barrier 135 may be fiber loaded or oil impregnated.

The first magnet 140 and the second magnet 142 may be any shape that provides a balanced mass during rotation. In some examples, the first magnet 140 and the second magnet 142 may be dipole magnets cylindrical in shape, with north and south poles disposed adjacent the opposing flat sides. The north pole of the first magnet 140 may be positioned across the fluid barrier 135 from the south pole of the second magnet 142 or the south pole of the first magnet 140 may be positioned across the fluid barrier 135 from the north pole of the second magnet 142. This orientation of the first and second magnets 140, 142 ensures that the attractive magnetic force between the magnets couples the rotational movement of the second magnet 142 with rotational movement of the first magnet 140. The magnetic force is transmitted through the fluid barrier 135. In use, the power source 195 rotates the drive shaft 190 thereby rotating the second magnet 142, which in turn causes the first magnet 140 to rotate at the same speed as the second magnet 142. Rotation of the first magnet 140 rotates the attached impeller shaft 150 which rotates the attached impeller 160. The impeller 160 may be in fluid contact with blood in the blood vessel, thus rotation of the impeller 160 may create suction to draw blood into the distal end 128 of the housing 120 and drive the blood out through the side openings 130, thereby increasing blood flow from the left ventricle into the ascending aorta when the device 110 is positioned as shown in FIG. 4. The fluid barrier 135 prevents blood leakage into the second section 122 of the housing 120 and thus prevents blood contact with the drive shaft 190 and the power source 195.

In other examples, the first magnet 140 and second magnet 142 may have more than two poles. Additionally, more than one dipole or multiple pole magnet may be positioned on either side of the fluid barrier 135. Regardless of the number and/or type of magnet used, the magnet(s) are configured and positioned such that rotation of the magnet(s)

connected to the drive shaft 190 and power source 195 causes rotation of the magnet(s) connected to the impeller 160.

Figure 6:
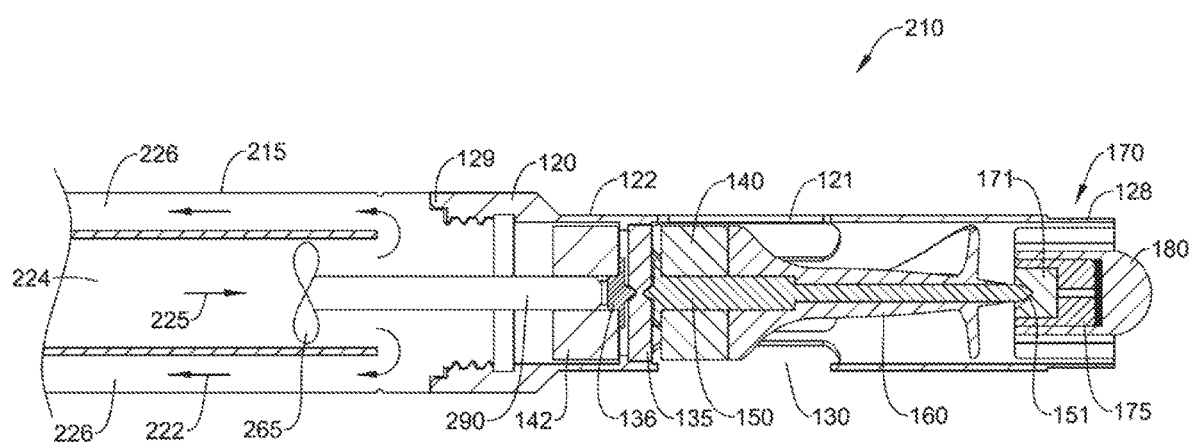
FIG. 6 is a cross sectional view of another exemplary device for assisting blood flow.

FIG. 6 illustrates another embodiment of a device 210 for assisting blood flow. The device 210 is similar to that illustrated in FIG. 5, but the power source is different. In device 110 illustrated in FIG. 5 the power source 195 is shown as an electric motor, whereas in device 210 the power source is a high or low pressure fluid, similar to the example mechanisms shown in FIGS. 2 and 3. The device 210 illustrated in FIG. 6 may include a catheter shaft 215 coupled to the proximal end 129 of the housing 120. The distal end of the drive shaft 290 may be connected to the second magnet 142 and the proximal end of the drive shaft 290 may be connected to a second impeller 265. The catheter shaft 215 may include an inner lumen 224 and an outer lumen 226. A high or low pressure fluid such as saline or other suitable fluid may be injected through the inner lumen 224 towards the second impeller 265, as shown by arrow 225. The high or low pressure fluid turns the second impeller 265, which rotates the drive shaft 290 and the attached second magnet 242. As in the device 110, rotation of the second magnet 142 causes the first magnet 140 to rotate, thereby rotating the impeller shaft 150 and the impeller 160. The impeller 160 is in contact with blood in the blood vessel, thus rotation of the impeller 160 assists blood flow through the blood vessel. After turning the second impeller 265, the high or low pressure fluid then returns through the outer lumen 226, as shown by arrows 222. The fluid is prevented from entering the blood vessel by the fluid barrier 135. Similarly, the fluid barrier 135 prevents blood from entering the catheter shaft 215 and mixing with the high or low pressure fluid. The high or low pressure fluid may be provided from a pressurized source outside the body, and the return fluid may be collected and recycled outside the body.

Alternatively, the direction of the fluid flow may be reversed, similar to that shown in FIG. 3. The high or low pressure fluid may be injected through the outer lumen 226 towards the second impeller 265. The high or low pressure fluid turns the second impeller 265, which rotates the drive shaft 290 and the attached second magnet 242 which causes the first magnet 140 to rotate, thereby rotating the impeller shaft 150 and the impeller 160. After turning the second impeller 265, the high or low pressure fluid then returns through the inner lumen 224.

Figure 7A:
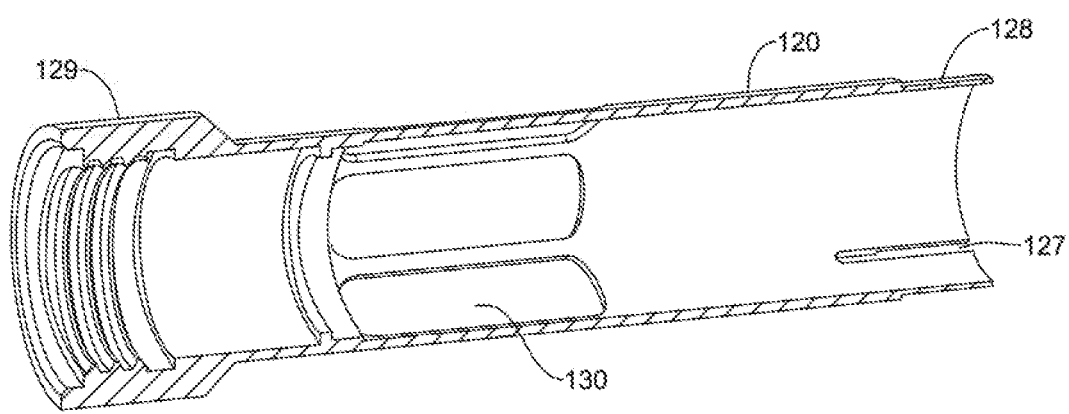
FIGS. 7A and 7B are cross sectional views of two different exemplary housings.
Figure 7B:
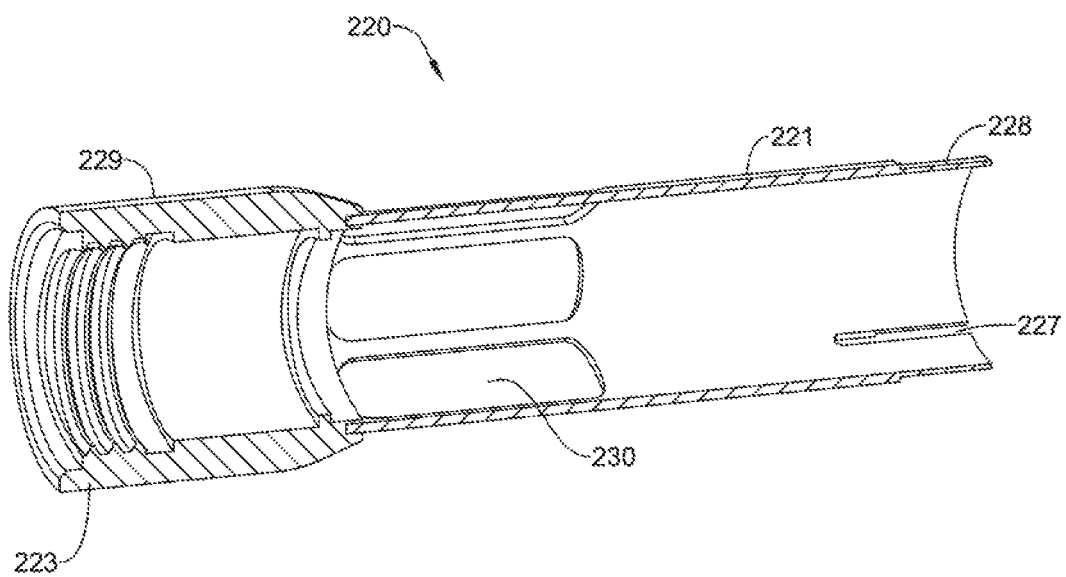

FIGS. 7A and 7B illustrate two examples of housings. A single part housing 120 is shown in FIG. 7A. The housing 120 may include a proximal end 129 configured to be coupled to a catheter shaft. In the embodiment shown in FIG. 7A, the proximal end 129 has internal threading. Alternatively, the proximal end 129 may connect to a catheter shaft with a snap fit, weld bond, adhesive bond, etc. The housing 120 may have at least one side opening 130 extending completely through the wall of the housing. When the housing 120 includes a plurality of side openings 130, the side openings 130 may be spaced apart around the circumference of the housing 120, as shown in FIG. 7A. The distal end 128 of the housing 120 may include at least one opening or slot 127 configured to connect with the bearing housing 180 shown in FIGS. 5 and 6.

A two part housing 220 is shown in FIG. 7B. The only difference in the two housing embodiments is in the number of parts. The two part housing 220 has a proximal portion 223 and a distal portion 221. As in the single part housing 120, the two part housing 220 has a proximal end 229 with internal threading, a plurality of side openings 230, and one or more slot 227 at the distal end 228 of the housing 220.

Figure 8:
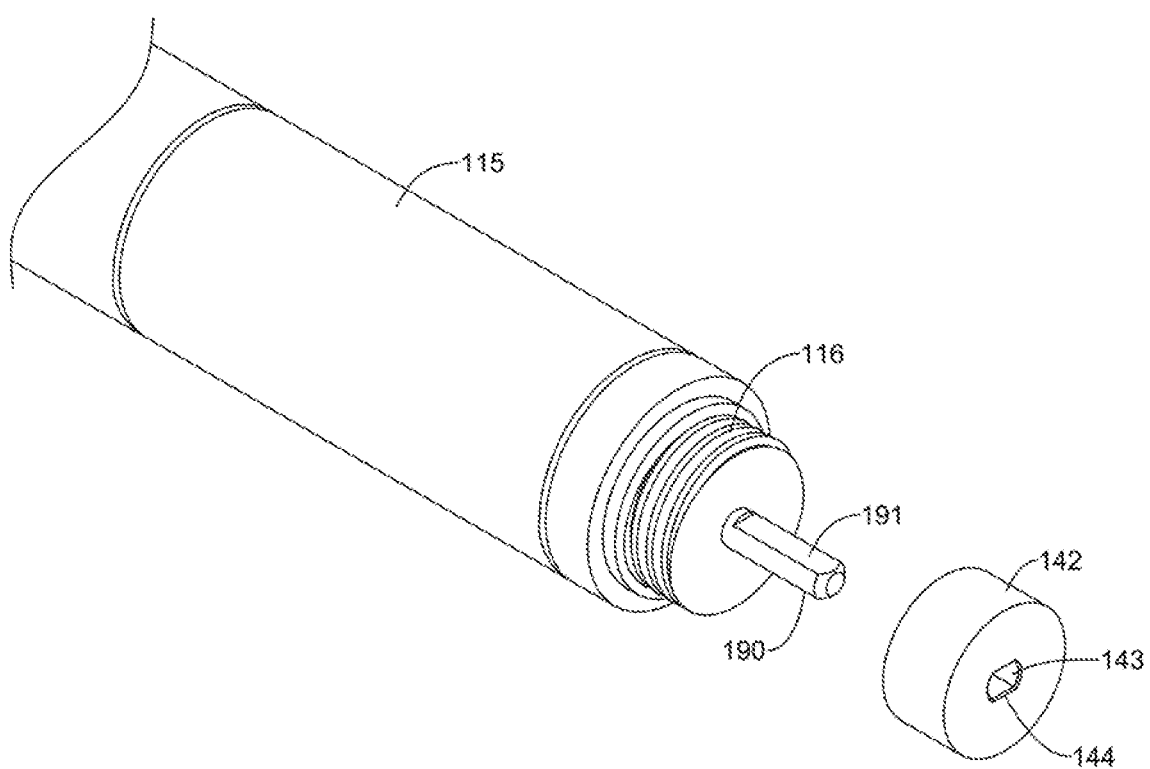
FIG. 8 is a partial perspective view of an exemplary catheter shaft, drive shaft, and second magnet.

FIG. 8 illustrates the distal end region of an example catheter shaft 115 and second magnet 142 and the structures providing their connection. The catheter shaft 115 may have threading 116 at the distal end thereof to engage the threaded proximal end 129, 229 of the housing 120, 220 shown in FIGS. 6A and 6B. Alternatively, the distal end of the catheter shaft 115 may connect to the proximal end of the housing with a snap fit or weld bond. The drive shaft 190 may be connected to a power source within the catheter shaft 115 and may have a non-round shape configured to mate with a non-round opening 143 through the second magnet 142. In some examples, the drive shaft 190 may have at least one flat surface 191 configured to engage at least one flat surface in the opening 143 through the second magnet 142. In the example device shown in FIG. 7, the drive shaft 190 has a transverse cross-sectional stadium shape with two opposing flat surfaces 191 that engage two opposing flat surfaces 144 in the opening 143 through the second magnet 142. The engagement between the flat surfaces 191 on the drive shaft 190 and the flat surfaces 144 in the opening 143 through the second magnet 142 allows for the second magnet 142 to be rotatably coupled to the drive shaft 190 while permitting some axial movement of the second magnet 142 relative to the drive shaft 190. The permitted axial movement of the second magnet allows the second magnet to be drawn toward the fluid barrier 135, allowing the attractive magnetic forces to be applied to fluid barrier 135, and reducing the axial load on the drive shaft 190 and power source. Although the example illustrated in FIG. 8 is of a shaft 190 with flat surfaces 191, it will be understood that the shaft 190 and opening 143 through the second magnet 142 may have any cross-section which allows both axial movement and rotational coupling between the drive shaft 190 and second magnet 142. Examples of suitable shapes may include a "D" shape, stadium shape, polygon, star, oval, ellipse, crescent, teardrop, etc.

Figure 9A:
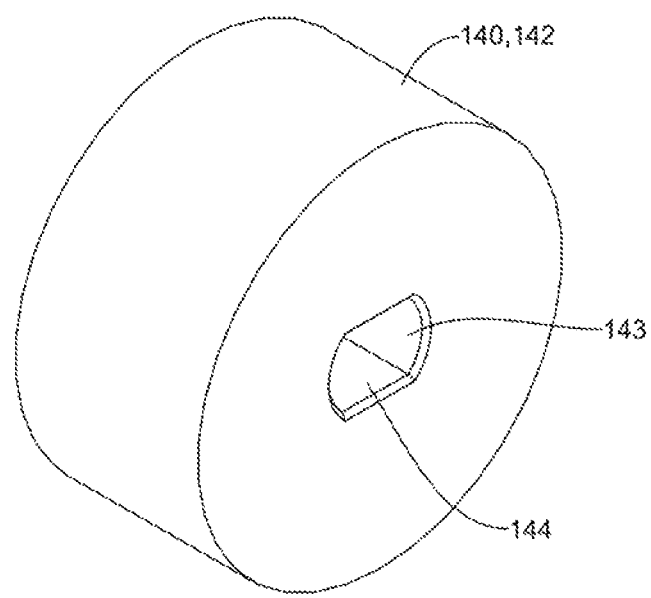
FIGS. 9A and 9B are perspective views of two different exemplary magnets.
Figure 9B:
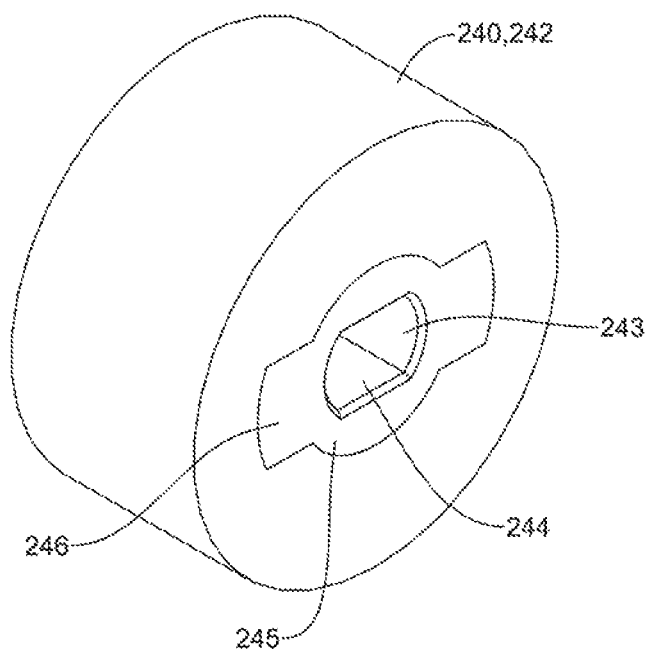
Figure 9C:
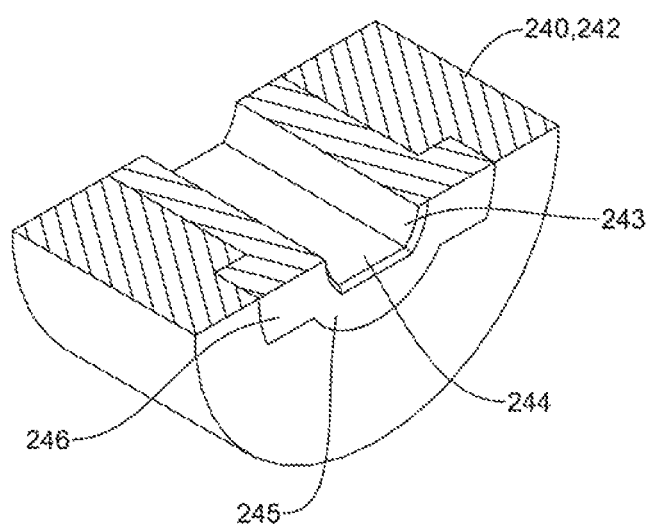
FIG. 9C is a cross sectional view of the magnet shown in FIG. 9B.

The first magnet 140 and second magnet 142 may be a single piece structure as illustrated in FIG. 9A. Alternatively, the first magnet 240 and/or second magnet 242 may have an insert 245 that defines the opening 243, as illustrated in FIGS. 9B and 9C. The insert 245 may be made of a non-magnetic or magnetic material. The insert 245 may include a locking feature such as tab 246 as shown in FIGS. 9B and 9C. For any of the first and second magnets 140, 142, 240, 242, the transverse cross-sectional shape of the opening 143, 243, taken perpendicular to the longitudinal axis of the drive shaft, may be any non-round shape that matches the transverse cross-sectional shape of the shaft on which the magnet resides. The non-round shape may help keep the shafts in balance when spinning at very high RPMs. In the example illustrated in FIGS. 8-10, the transverse cross-sectional shape of the openings 143, 243 is a stadium, which is a rectangle with semicircles at opposite ends. The stadium shape of the opening 143, 243, particularly the opposing flat surfaces 144, 244, mates with a flat sided impeller shaft 150 or drive shaft 190.

Figure 10:
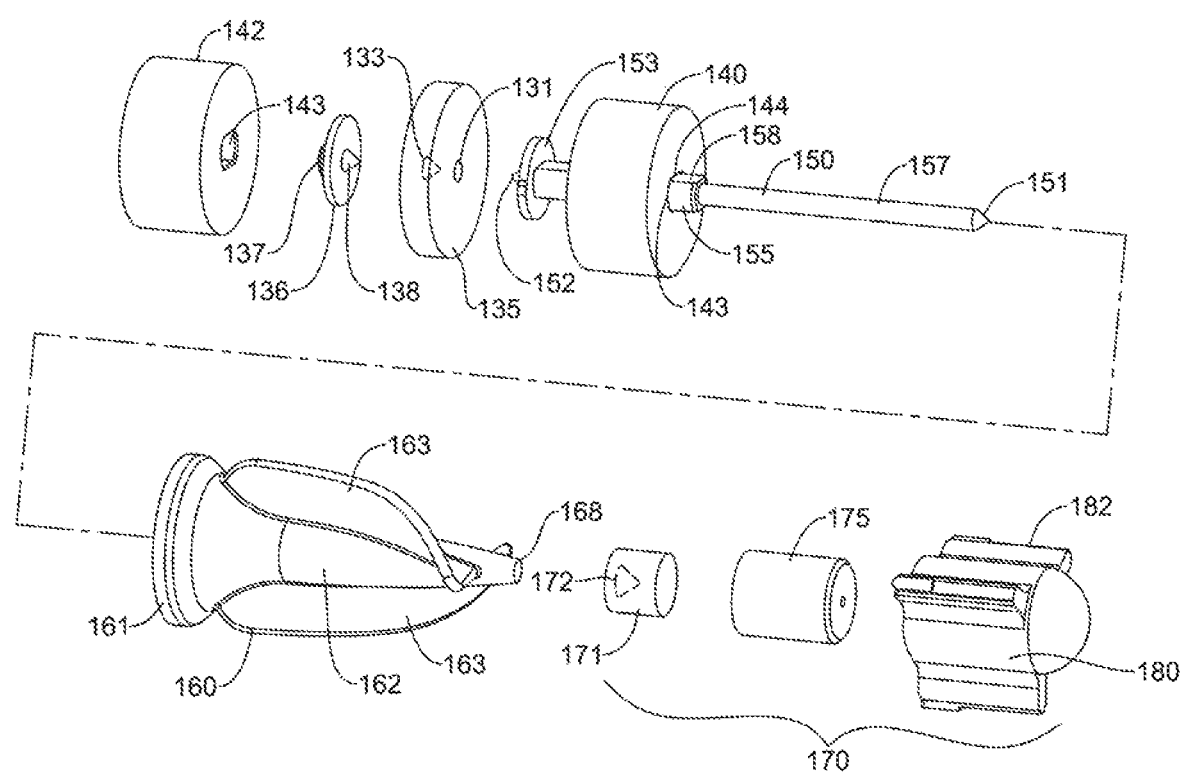
FIG. 10 is a partial perspective exploded view of an exemplary device for assisting blood flow.

The internal components of the device 110 shown in FIG. 5 are illustrated in an exploded perspective view in FIG. 10. The pivot member 136 may serve as a spacer between the rotating second magnet 142 and the stationary fluid barrier 135, and directs the attractive magnetic forces to fluid barrier 135, preventing wear on the second magnet 142 and reducing the axial loads on the drive shaft and power source. The pivot member 136 may have a proximal protrusion 137 shaped to be received in the opening 143 in the second magnet 142. The shape of the proximal protrusion 137 and the shape of the opening 143 in the second magnet 142 are non-round, ensuring rotation of the proximal protrusion 137 with rotation of the second magnet 142. In some examples, the proximal protrusion 137 may be stadium shaped and configured to be received in the stadium shaped opening 143 in the second magnet 142. The mating of the proximal protrusion 137 within the opening 143 causes the pivot member 136 to rotate with the second magnet 142. The pivot member 136 may have a distal projection 138 extending from the bearing surface and shaped to be received in a proximal recess 133 in the fluid barrier 135. The distal projection 138 and the proximal recess 133 are shaped such that when the distal projection 138 is seated in the proximal recess 133, the pivot member 136 rotates against the stationary fluid barrier 135. The distal projection 138 and proximal recess 133 may be conical in shape as illustrated in FIG. 10. Alternatively, the distal projection 138 and proximal recess 133 may be spherical. In another example, the pivot member 136 may have a recess in the distal surface shaped to mate with a proximal protrusion on the fluid barrier 135. The pivot member 136 may be made of a material that slides against the fluid barrier 135 with minimal friction. For example, the pivot member 136 may be made of ceramic, zirconia, alumina, cobalt chromium alloys, titanium alloys such as nitinol, hardened steel, material such as metal, ceramic or polymer coated with diamond-like carbon (DLC) or titanium nitride. In some examples, a lubricant may be added to the proximal or bearing surface of the pivot member 136.

The impeller shaft 150 may have a proximal protrusion 152 shaped to mate with a distal recess 131 in the fluid barrier 135. Similar to the distal projection 138 on the pivot member and the proximal recess 133, the proximal protrusion 152 and distal recess 131 are shaped such that when the proximal protrusion 152 is seated in the distal recess 131, the impeller shaft 150 rotates against the stationary fluid barrier 135. The proximal protrusion 152 and distal recess 131 may be conical shaped, as illustrated in FIG. 10, or they may be spherical in shape. The proximal protrusion 152 protrudes from a disc 153 that extends perpendicularly from the longitudinal axis of the impeller shaft 150. Alternatively, the impeller shaft 150 may have a recess in the proximal surface of the disc 153 shaped to mate with a distal protrusion on the fluid barrier 135.

The disc 153 serves as a spacer between the rotating first magnet 140 and the stationary fluid barrier 135, preventing wear on the first magnet 140. The disc 153 positions the first magnet 140 the desired distance from the second magnet 142. In some examples, this distance may be between 0.01 mm and 3.00 mm. As with the pivot member 136, the proximal protrusion 152 and disc 153 of the impeller shaft 150 may be made of a material that slides against the fluid barrier 135 with minimal friction. The impeller shaft 150 may have a proximal region 155 shaped to be received within the opening 143 in the first magnet 140. The proximal region 155 passes through the first magnet 140 and into the impeller 160. Similar to the drive shaft 190 discussed above, the proximal region 155 of the impeller shaft 150 may have any non-round transverse cross-sectional shape that matches a non-round transverse cross-sectional shape of the opening 143 in the first magnet 140. In the example illustrated in FIG. 10, the proximal region 155 of the impeller shaft 150 has a transverse cross-sectional stadium shape with opposing flat surfaces 158 that mate with the flat surfaces 144 in the opening 143 in the first magnet 140, thereby mechanically affixing the first magnet 140 to the impeller shaft 150 for the transfer of torque. The flat surfaces 158 may keep the impeller shaft 150 balanced for smooth, vibration-free spinning. Extending the flat surfaces 158 of the impeller shaft 150 into the impeller 160 locks the impeller 160 to the first magnet 140. The distal region 157 of the impeller shaft 150 may be cylindrical.

The impeller 160 may have a base 161, a main body 162, and at least one blade 163. In the example illustrated in FIG. 10, the impeller 160 has two opposing blades 163. In other examples, 3, 4, or more blades may be present. It will be understood that the shape of the blades 163 is illustrative and that other shapes of blades 163 may be provided. The impeller 160 may be positioned in the housing 120 such that the blades 163 are adjacent the side openings 130. The blades 163 may be shaped such that rotation of the impeller 160 creates suction to draw blood into the housing 120 through the distal end 128 of the housing 120 and drive the blood out through the side openings 130. Alternatively, the blades 163 may be shaped and configured such that rotation of the impeller 160 draws blood into the housing 120 through the side openings 130 and drives the blood out through the distal end 128 of the housing. In some examples, the shape of the blades 163 may be opposite that illustrated in FIG. 10. The impeller 160 may have a distal opening 168 through which the distal end 151 of the impeller shaft 150 extends. The distal end 151 of the impeller shaft 150 may be shaped to mate with the distal bearing assembly 170 that is fixed to the distal end 128 of the housing 120, as shown in FIG. 5.

In the example illustrated in FIG. 10, the impeller 160 is a structure separate from the impeller shaft 150 and coupled to the impeller shaft 150. In other examples, the impeller 160 may be fixedly attached to the impeller shaft 150 by bonding, welding, molding, etc. Alternatively, the impeller 160 and impeller shaft 150 may be formed as a single monolithic structure. In further examples, the impeller may be formed of blades 163 coupled directly to the impeller shaft 150, such as by bonding, welding, molding, etc. Alternatively, the blades 163 and impeller shaft 150 may be formed as a single monolithic structure.

The distal bearing assembly 170 may include the distal bearing 171, spacer 175, and bearing housing 180. The distal end 151 of the impeller shaft 150 may be received in a recess 172 within the distal bearing 171. In the example shown in FIG. 10, the distal end 151 of the impeller shaft 150 and the recess 172 are conical in shape. Alternatively, the distal end 151 of the impeller shaft 150 and the recess 172 may be spherical in shape. The distal bearing 171 may be made of a material that allows the impeller shaft 150 to turn against it with minimal friction. The distal bearing 171 may be fixed to the spacer 175 which may slide axially within the bearing housing 180. The bearing housing 180 may be fixed to the housing 120. The bearing housing 180 may have at least one fin 182 extending radially outward and configured to mate with the slot 127 in the housing 120, shown in FIG. 7A. The distal bearing assembly 170 centers the impeller shaft 150 in the housing 120, with the longitudinal axis of the impeller shaft 150 aligned with the longitudinal axis of the housing 120. The distal bearing assembly 170 may allow for limited axial movement of the impeller shaft 150 within the housing 120.

Figure 11:
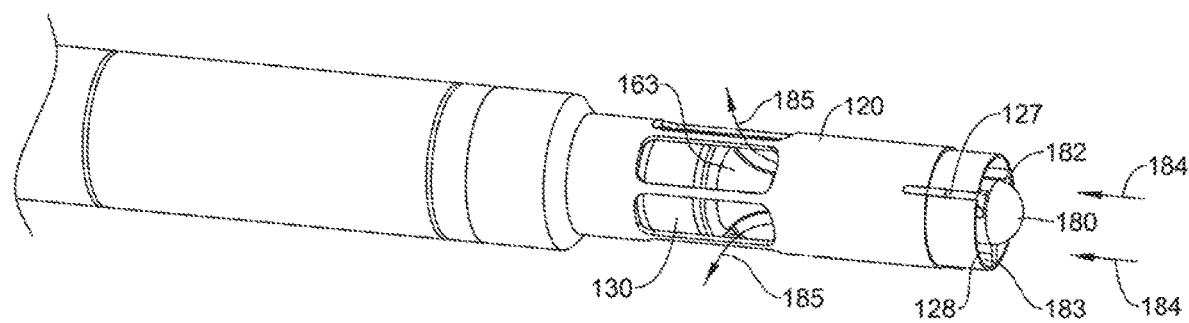
FIG. 11 is a partial perspective view of an exemplary device for assisting blood flow.

FIG. 11 illustrates the device of FIG. 10 assembled. As shown in FIG. 11, the fins 182 of the bearing housing 180 are configured such that when they are attached to the slots 127 in the housing 120, blood may flow into the distal end 128 of the housing 120 between the fins 182. Blood flow is indicated by arrows 184. Blood flows into the spaces 183 between adjacent fins 182 and through the interior of housing 120. Rotating impeller blades 163 drive blood flow out the side openings 130, indicated by arrows 185.

Figure 12:
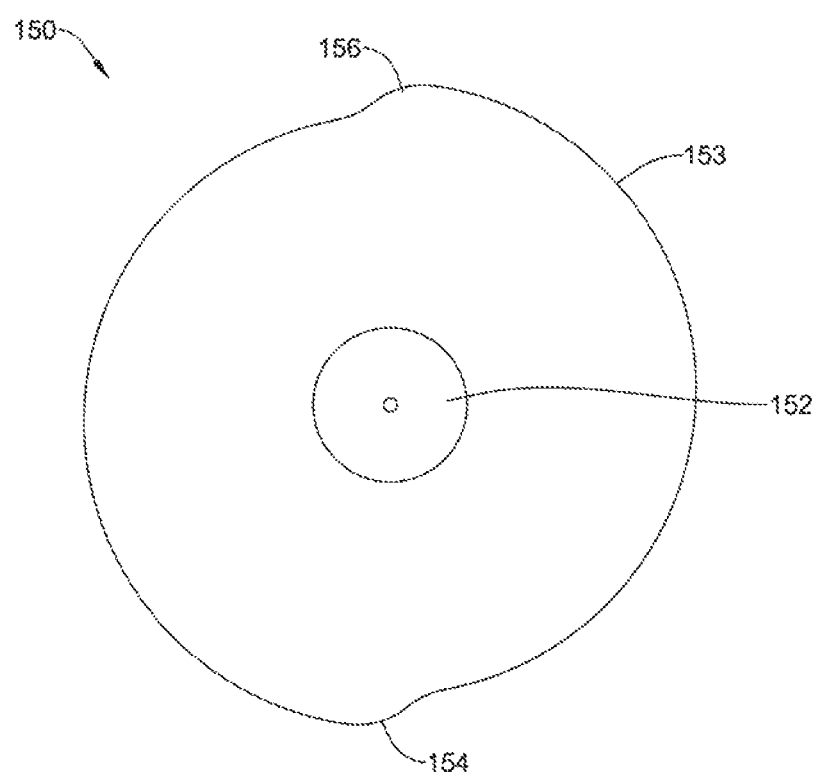
FIG. 12 is a proximal end view of an exemplary impeller shaft.

FIG. 12 is a proximal end view of an example impeller shaft 150, showing the structure of the disc 153. The disc 153 may have two opposing ramped grooves or lobes 154, 156 that create outward-directed turbulence to clear any blood that may otherwise tend to pool between the first magnet 140 and the fluid barrier 135.

Figure 13:
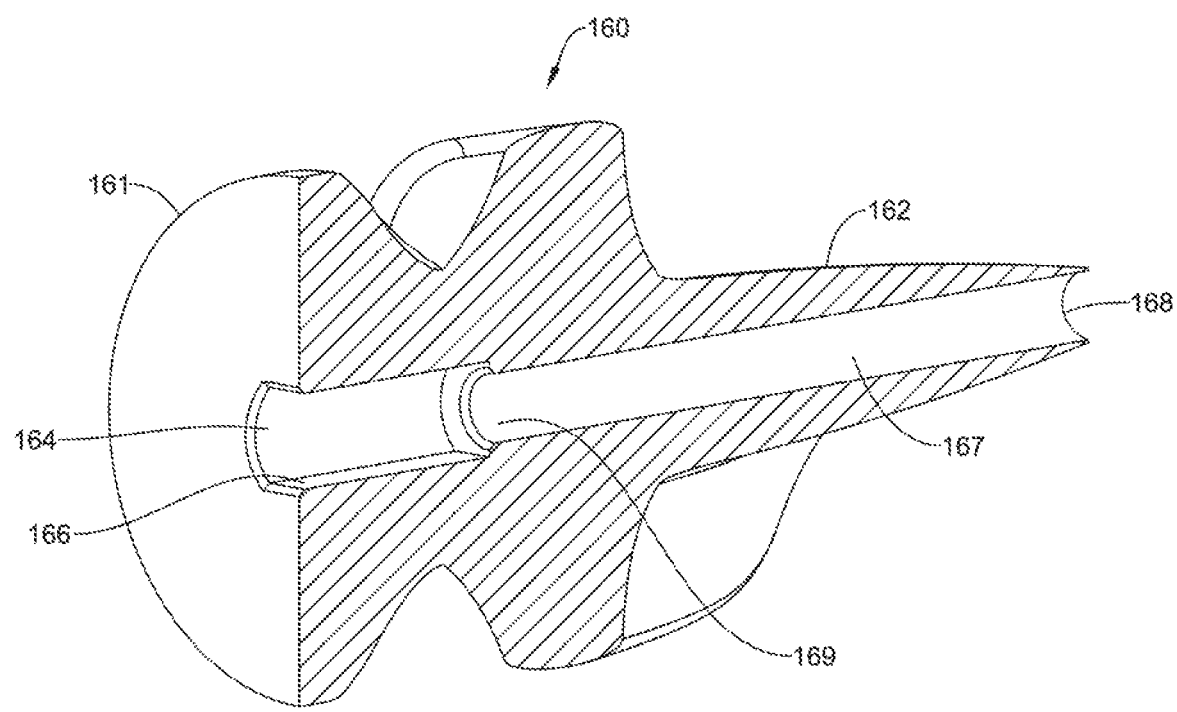
FIG. 13 is a perspective cross sectional view of an exemplary impeller.

Details of the internal structure of the impeller 160 are illustrated in FIG. 13. The impeller 160 may have a central channel 169 extending along the longitudinal axis of the impeller 160. A first region 164 of the channel 169 may extend through the base 161 and a second region 167 of the channel 169 may extend through the main body 162. The first region 164 may be shaped to receive the proximal region 155 of the impeller shaft 150. In the example illustrated in FIG. 13, the first region 164 is stadium shaped, with opposing flat sides 166 that mate with the flat surfaces 158 of the impeller shaft 150. The second region 167 may be round to mate with the round distal region 157 of the impeller shaft 150. The central channel 169 ends at distal opening 168.

Figure 14:
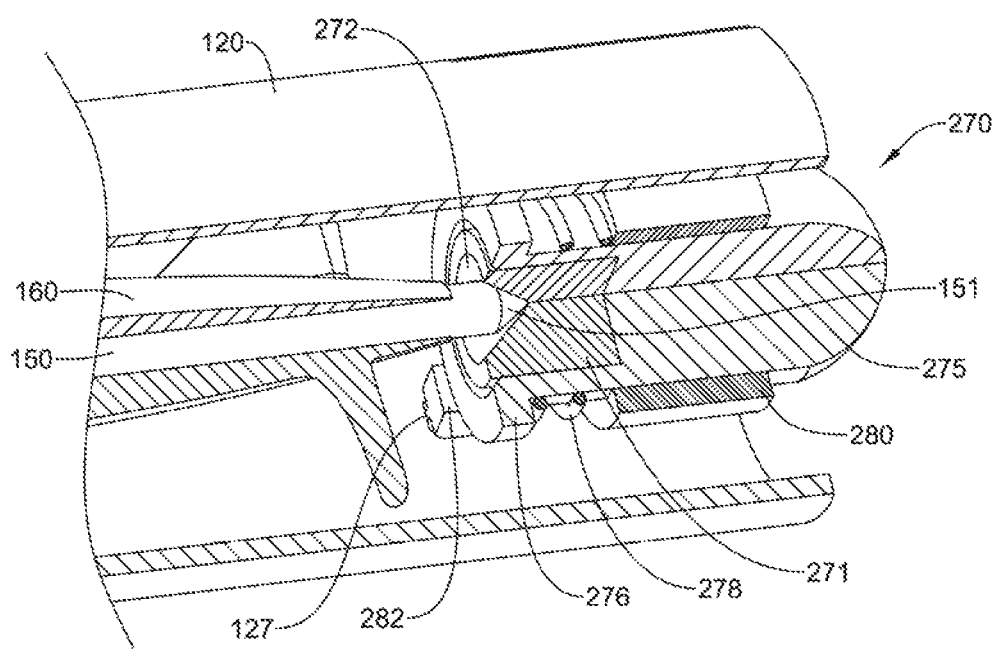
FIG. 14 is a partial cut-away view of an exemplary distal bearing assembly.

FIG. 14 illustrates an alternative distal bearing assembly 270 disposed within the distal end of the housing 120. The distal bearing assembly 270 may include a distal bearing 271, spacer 275, and bearing housing 280. The distal end 151 of the impeller shaft 150 may be received in a recess 272 within the distal bearing 271. In the example shown in FIG. 14, the distal end 151 of the impeller shaft 150 and the recess 272 are conical in shape, with the recess 272 being significantly larger than the distal end 151 of the impeller shaft 150. Alternatively, the distal end 151 of the impeller shaft 150 and the recess 272 may be spherical in shape. The distal bearing 271 may be made of a material that allows the impeller shaft 150 to turn against it with minimal friction. The distal bearing 271 may be imbedded within the spacer 275. The spacer 275 may slide axially within the bearing housing 280. The spacer 275 may have a proximal ridge 276. A spring member 278 may be positioned circumferentially around an outer surface of the spacer 275, between the proximal ridge 276 and the bearing housing 280. The spring member 278 may provide a light but constant pressure on the impeller shaft 150, maintaining the impeller shaft 150 centered within the housing 120 and allowing the impeller shaft 150 to rotate smoothly. In some examples, the spring member 278 may be metal. In other examples, the spring member 278 may be made of an elastic material. The bearing housing 280 may be fixed to the housing 120. The bearing housing 280 may have at least one fin 282 configured to mate with the slots 127 in the housing 120.

The materials that can be used for the various components of the device 110, 210 for assisting blood flow (and/or other systems or components disclosed herein) and the various elements thereof disclosed herein may include those commonly associated with medical devices. For simplicity purposes, the following discussion makes reference to the device 110, 210 (and variations, systems or components disclosed herein). However, this is not intended to limit the devices and methods described herein, as the discussion may be applied to other elements, members, components, or devices disclosed herein.

In some embodiments, the device 110, 210 (and variations, systems or components thereof disclosed herein) may be made from a metal, metal alloy, ceramics, zirconia, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the device 110, 210 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the device 110, 210 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the device 110, 210 (and variations, systems or components thereof disclosed herein) to achieve the same result.

In some embodiments, the device 110, 210 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the device 110, 210 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

The invention claimed is:

1. A medical device for implantation within a heart of a patient, the medical device comprising:
   a housing including at least one inlet for receiving blood flow, and at least one outlet for delivering blood flow, the housing having a longitudinal axis and being sized for placement within the heart;
   a fluid barrier disposed within the housing and separating the housing into a first section containing the at least one inlet and the at least one outlet, and a second section, the fluid barrier being impervious to fluid;
   an impeller disposed within the first section of the housing, wherein a longitudinal axis of the impeller and the longitudinal axis of the housing are the same, the impeller having a main body and at least one blade extending radially outward from the main body;

at least a first magnet coupled to an impeller shaft, the impeller shaft coupled to the impeller, the first magnet disposed in the first section of the housing and rotatably coupled to the impeller shaft;

a drive shaft disposed within the second section of the housing;

at least a second magnet disposed on the drive shaft within the second section of the housing, the first and second magnets configured and arranged such that rotation of the second magnet causes the first magnet to rotate and such that the second magnet is rotatably coupled to the drive shaft while permitting axial movement of the second magnet along the drive shaft to allow the second magnet to be drawn toward the fluid barrier to thereby allow attractive magnetic forces to be applied to the fluid barrier and to reduce axial loads on the drive shaft; and a pivot member arranged longitudinally between the second magnet and the fluid barrier, the pivot member having a non-round proximal protrusion configured for engagement with a non-round opening of the second magnet such that rotation of the second magnet causes rotation of the pivot member, and the pivot member further having a round distal protrusion for engagement with a round opening of the fluid barrier such that the pivot member is rotatable against the fluid barrier.

2. The medical device of claim 1, further comprising a power source coupled to the drive shaft, and wherein permitting axial movement of the second magnet reduces axial loads on the power source.

3. The medical device of claim 2, wherein the power source is disposed within a catheter shaft attached to the second section of the housing.

4. The medical device of claim 3, wherein the power source is a motor.

5. The medical device of claim 3, wherein the power source is a second impeller connected to the drive shaft, wherein the catheter shaft defines a fluid pathway, wherein the drive shaft and second impeller are disposed within the fluid pathway such that a fluid impacting the second impeller drives the impeller which turns the second magnet, which causes the first magnet to turn, thereby turning the impeller shaft and impeller.

6. The medical device of claim 1, wherein the at least one outlet includes a plurality of side openings spaced apart around a circumference of the housing, wherein the impeller is positioned within the housing such that the at least one blade is disposed adjacent the plurality of side openings.

7. The medical device of claim 1, wherein a proximal end of the impeller shaft extends proximal of the first magnet, the proximal end having a first protrusion configured to be received by a first recess in the fluid barrier.

8. The medical device of claim 7, wherein the impeller shaft includes a disc adjacent the first protrusion, the disc extending perpendicularly from a longitudinal axis of the impeller shaft.

9. The medical device of claim 8, wherein the disc has two opposing lobes.

10. The medical device of claim 1, further comprising a bearing assembly configured to support and center a distal end of the impeller shaft, the bearing assembly including a bearing housing fixed to the housing, a spacer slidably disposed within the bearing housing, and a distal bearing fixed within the spacer.

11. The medical device of claim 10, wherein the bearing assembly further includes a spring member disposed around the spacer.

12. The medical device of claim 1, wherein the drive shaft is configured to be rotated within the second section of the housing to thereby rotate the second magnet, which causes rotation of the first magnet, to thereby rotate the impeller shaft and the impeller so as to create a suction that allows the device to, when placed in the ascending aorta, draw blood from the left ventricle through the at least one inlet into the housing and to drive blood through the at least one outlet and into the ascending aorta.

13. The medical device of claim 1, wherein the fluid barrier functions as a thrust bearing against which the pivot member is rotatable.

14. A medical device for implantation within a body of a patient, comprising:

a housing including an inlet for receiving blood flow, and a plurality of side openings for delivering blood flow, the housing having a longitudinal axis and being sized for placement within the heart;

a fluid barrier disposed within the housing and separating the housing into a first section containing the inlet and the plurality of side openings, and a second section, the fluid barrier being impervious to fluid;

an impeller disposed within the first section of the housing, wherein a longitudinal axis of the impeller and the longitudinal axis of the housing are the same, the impeller having a main body and at least one blade extending radially outward from the main body;

at least a first magnet disposed in the first section of the housing and coupled to the impeller such that rotation of the first magnet causes rotation of the impeller;

a drive shaft disposed within the second section of the housing, the drive shaft having a stop surface and at least one flat surface extending from the stop surface;

at least a second magnet coupled to the drive shaft and disposed within the second section of the housing, the first and second magnets configured and arranged such that rotation of the second magnet causes rotation of the first magnet and such that the second magnet is rotatably coupled to the drive shaft while permitting axial movement of the second magnet along the drive shaft between the stop surface of the drive shaft and a spacer arranged between the second magnet and the fluid barrier, to allow the second magnet to be drawn toward the fluid barrier to thereby allow attractive magnetic forces to be applied to the fluid barrier and reduce axial loads on the drive shaft and a power source;

wherein the first magnet has a first opening therethrough configured for receiving and coupling the impeller shaft to the first magnet, the second magnet has a second opening therethrough configured for receiving and coupling the drive shaft to the second magnet, wherein the first and second openings each have a first transverse cross-sectional shape taken perpendicular to a longitudinal axis of the drive shaft; and wherein the drive shaft and at least a portion of the impeller shaft each have a second transverse cross-sectional shape taken perpendicular to the longitudinal axis of the respective shafts, wherein the first and second transverse cross-sectional shapes are non-round, such that rotation of the impeller shaft and drive shaft causes rotation of the first and second magnets, respectively.

15. The medical device of claim 14, wherein the medical device further includes a catheter shaft, wherein the power source is a second impeller connected to the drive shaft, wherein the catheter shaft defines a fluid pathway, wherein the drive shaft and second impeller are disposed within the fluid pathway such that a fluid impacting the second impeller drives the impeller which turns the second magnet, which causes the first magnet to turn, thereby turning the impeller.

16. The medical device of claim 14, further comprising an impeller shaft disposed within and coupled to the impeller and the first magnet, and a bearing assembly configured to support and center a distal end of the impeller shaft, the bearing assembly including a bearing housing fixed to the housing, a spacer slidably disposed within the bearing housing, and a distal bearing fixed within the spacer.

17. A medical device for implantation within a heart of a patient, the medical device comprising:
- a housing including at least one inlet for receiving blood flow, and at least one outlet for delivering blood flow, the housing having a longitudinal axis and being sized for placement within the heart;
- a fluid barrier disposed within the housing and separating the housing into a first section containing the at least one inlet and the at least one outlet, and a second section, the fluid barrier being impervious to fluid, the first barrier having a first side opposite a second side;
- an impeller disposed within the first section of the housing, wherein a longitudinal axis of the impeller and the longitudinal axis of the housing are the same;
- a drive shaft disposed within the second section of the housing;
- a first magnet coupled to an impeller shaft, the impeller shaft coupled to the impeller, the first magnet disposed in the first section of the housing and rotatably coupled to the impeller shaft;
- a second magnet disposed on the drive shaft within the second section of the housing, the first and second magnets configured and arranged such that rotation of the second magnet causes the first magnet to rotate and such that the second magnet is rotatably coupled to the drive shaft;
- a disc coupled with the impeller shaft, the disc having a protrusion extending from the disc;
- a pivot member arranged between the fluid barrier and the second magnet, the pivot member having at least one protrusion extending from the pivot member; and
- wherein the at least one protrusion of the pivot member is configured for engagement with the second side of the fluid barrier and the at least one protrusion of the disc is configured for engagement with the first side of the fluid barrier, such that the fluid barrier functions as a thrust bearing against which the pivot member and the disc, and therefore the impeller shaft, rotate.

18. The medical device of claim 17, wherein the disc is formed of a material configured to allow sliding against the fluid barrier with a minimal amount of friction.

19. The medical device of claim 17, further comprising a distal bearing assembly disposed at the distal end of the housing, the distal bearing assembly including a distal bearing configured for receiving a portion of the impeller shaft, a spacer fixed with the distal bearing, and a bearing housing fixed with the housing of the medical device, wherein the spacer is configured to slide axially within the bearing housing.

20. The medical device of claim 19, wherein the distal bearing has a recess for receiving a distal end of the impeller shaft and wherein the distal end of the impeller shaft and the recess of the distal bearing are conical in shape.

21. The medical device of claim 19, wherein the bearing housing has at least one fin extending radially outward, the housing having at least one slot, and wherein the at least one fin of the bearing housing is received within the at least one lot of the housing.

22. The medical device of claim 19, wherein the bearing assembly further includes a spring member positioned circumferentially around an outer surface of the spacer configured to maintain the impeller shaft in a centered positioned within the housing.

* * * * *